US012766277B2

(12) United States Patent
Gerstenmeier

(10) Patent No.: US 12,766,277 B2
(45) Date of Patent: Oct. 20, 2026

(54) USE OF CANNABINOIDS IN THERAPY AND WELL-BEING APPARATUSES

(71) Applicant: JK-HOLDING GMBH, Windhagen (DE)

(72) Inventor: Jürgen Gerstenmeier, Neuwied (DE)

(73) Assignee: JK-HOLDING GMBH, Windhagen (DE)

( * ) Notice: Subject to any disclaimer, the term of this patent is extended or adjusted under 35 U.S.C. 154(b) by 856 days.

(21) Appl. No.: 17/930,531

(22) Filed: Sep. 8, 2022

(65) Prior Publication Data

US 2023/0001113 A1 Jan. 5, 2023

Related U.S. Application Data

(63) Continuation of application No. PCT/IB2021/051983, filed on Mar. 10, 2021.

(30) Foreign Application Priority Data

Mar. 11, 2020 (CH) .................................... 00276/20

(51) Int. Cl.
*A61M 15/00* (2006.01)
*A24F 40/10* (2020.01)
*A61M 11/04* (2006.01)

(52) U.S. Cl.
CPC ......... *A61M 15/0086* (2013.01); *A24F 40/10* (2020.01); *A61M 11/042* (2014.02)

(58) Field of Classification Search
CPC ............ A61M 15/0086; A61M 11/042; A61M 15/0065; A61M 21/00; A61M 21/0094;
(Continued)

(56) References Cited

U.S. PATENT DOCUMENTS 3,877,691 A * 4/1975 Foster ................. A61M 16/009
128/200.24
3,902,488 A 9/1975 Sheppard
(Continued)

FOREIGN PATENT DOCUMENTS

CA 2668217 A1 4/2010
CN 1064803 A 9/1992
(Continued)

OTHER PUBLICATIONS

Taiwan Intellectual Property Office Search Report, created Feb. 13, 2025. 3 pages (w/ translation).
(Continued)

*Primary Examiner* — Elliot S Ruddie
(74) *Attorney, Agent, or Firm* — HESLIN ROTHENBERG FARLEY & MESITI P.C.

(57) ABSTRACT

The present invention relates to a device for applying energy to a human body. The device comprises a contact surface which defines an application region in which a human body can be placed in the effective range of the energy. The device further comprises at least one means for outputting the energy directed substantially onto the application region, and at least one means for generating a vapour mixture comprising at least one cannabinoid. The device according to the invention also comprises at least one means for guiding the vapour mixture, which has an effective dose of at least one cannabinoid, into the surroundings of the breathing orifices of a human body. The present invention further relates to a method for operating such a device, and to the use of vapour mixtures comprising at least one cannabinoid in designated devices.

20 Claims, 3 Drawing Sheets

(58) Field of Classification Search

CPC .............. A61M 11/005; A61M 11/041; A61M 16/0627; A61M 16/18; A61M 2021/0016; A61M 2230/65; A61M 15/0001; A61M 2021/0044; A61M 2021/0077; A61M 16/009; A61M 16/01; A61M 16/04; A61M 16/0463; A61M 16/0672; A61M 16/0816; A61M 16/1005; A61M 16/1055; A61M 2016/0413; A61M 21/02; A61M 2202/0241; A61M 2202/203; A61M 2202/206; A61M 2205/053; A61M 2230/432; A61M 15/08; A61M 16/0078; A61M 16/0087; A61M 16/0093; A61M 16/0434; A61M 16/0488; A61M 16/06; A61M 16/0891; A61M 16/106; A61M 16/1065; A61M 2016/103; A61M 2202/0208; A61M 2202/0225; A61M 2207/10; A61M 2210/005; A61M 2210/1053; A24F 40/10; A61N 5/0614; A61N 5/0618; A61N 2005/0637; A61N 2005/064; A61N 2005/0661; A61N 2005/0668; A61N 5/062; A61N 5/0616; A61H 2201/0142; A61H 2201/0149; A61H 2201/0188; A61H 2201/10; A61H 2201/105; A61H 2201/107; A61H 2201/5058; A61H 2201/5092; A61H 2203/0456; A61H 2205/02; A61H 2205/081; A61H 2230/08; A61H 2230/65; A61H 33/12; A61H 35/008; A61H 2009/0035; A61H 2033/068; A61H 2201/1654; A61H 2203/0431; A61H 2205/08; A61H 2230/42; A61H 2230/70; A61H 9/0021; A61K 31/352; A61G 10/005; A61G 10/02; A61G 13/108; A61G 13/1215; A61G 2210/00; A61G 10/00; A61C 17/0208; A61B 90/05

See application file for complete search history.

(56) References Cited

U.S. PATENT DOCUMENTS

| | | | | |
|---|---|---|---|---|
| 3,949,743 | A | 4/1976 | Shanbrom | |
| 6,497,717 | B1 | 12/2002 | Daffer et al. | |
| 9,271,894 | B2 | 3/2016 | Nakamura | |
| 9,440,041 | B1 | 9/2016 | LaCayo | |
| 10,299,515 | B2 | 5/2019 | Krietzman | |
| 2003/0156831 | A1 | 8/2003 | Schaeffer et al. | |
| 2004/0260364 | A1* | 12/2004 | Daffer | A61H 9/00 607/81 |
| 2005/0171451 | A1* | 8/2005 | Yeo | A61B 5/117 600/509 |
| 2009/0044311 | A1 | 2/2009 | Lipponen | |
| 2012/0167878 | A1* | 7/2012 | Belson | A61M 16/12 128/200.14 |
| 2013/0305448 | A1 | 11/2013 | Nguyen | |
| 2016/0271013 | A1 | 9/2016 | Jaguan | |
| 2017/0348276 | A1 | 12/2017 | Bryson et al. | |
| 2018/0168237 | A1* | 6/2018 | Krietzman | A61M 15/06 |
| 2018/0318529 | A1 | 11/2018 | Davidson et al. | |
| 2019/0105227 | A1 | 4/2019 | Mcneil | |
| 2019/0125988 | A1 | 5/2019 | Trzecieski | |
| 2019/0209801 | A1 | 7/2019 | Kimble et al. | |
| 2022/0054690 | A1 | 2/2022 | Wallach et al. | |

FOREIGN PATENT DOCUMENTS

| | | | |
|---|---|---|---|
| CN | 2286052 | Y | 7/1998 |
| CN | 2342821 | Y | 10/1999 |
| CN | 2745562 | Y | 12/2005 |
| CN | 2887296 | Y | 4/2007 |
| CN | 204364411 | U | 6/2015 |
| CN | 107982044 | A | 5/2018 |
| CN | 108992340 | A | 12/2018 |
| CN | 110433072 | A | 11/2019 |
| DE | 19633401 | A1 | 2/1998 |
| DE | 10014281 | A1 | 12/2001 |
| DE | 202017107690 | U1 | 3/2018 |
| JP | 2003180839 | A | 7/2003 |
| JP | 2004180981 | A | 7/2004 |
| JP | 2005102919 | A | 4/2005 |
| JP | 2010246787 | A | 11/2010 |
| TW | 201627896 | A | 8/2016 |
| WO | WO200236063 | A2 | 11/2001 |
| WO | 0236063 | A2 | 5/2002 |
| WO | 2003034971 | A2 | 5/2003 |
| WO | 2004100852 | A2 | 11/2004 |
| WO | 2005120428 | A1 | 12/2005 |
| WO | 2017118980 | A1 | 7/2017 |
| WO | 2017208072 | A2 | 12/2017 |
| WO | WO2019134851 | A1 | 7/2019 |

OTHER PUBLICATIONS

China National Intellectual Property Administration, First Office Action, mailed Oct. 8, 2024. 18 pages (w/ translation).

Republic of Colombia Superintendency of Industry and Commerce, Office Action, mailed Mar. 31, 2025. 19 pages (w/ translation).

Japan Patent Office, "Notice of Reasons For Rejection" issued in JP Application 2022-552443, mailed Jan. 7, 2025. 13 pages (w/ translation).

China National Intellectual Property Administration, "Second Office Action" issued in CN Application 202180025034.4, mailed Feb. 17, 2025. 14 pages (w/translation).

Guo, Wanxue et al.; "Physical Therapy", Beijing: People's Health Publishing House, Mar. 31, 1984, pp. 946-947.

"Clinical Technical Operation Specifications", Clinical Department of Tongling Municipal Hospital, Apr. 3, 2015, p. 160.

* cited by examiner

USE OF CANNABINOIDS IN THERAPY AND WELL-BEING APPARATUSES

CROSS REFERENCES TO RELATED APPLICATIONS

This application is based on, and claims priority to: PCT Patent Application No. PCT/IB2021/051983, filed on Mar. 10, 2021 and published as PCT Publication No. WO2021/181296A1; and Swiss Patent Application No. CH 00276/20, filed on Mar. 11, 2020. The contents of the prior patent applications are hereby incorporated by reference herein in their entirety.

TECHNICAL FIELD

The present invention relates to a device for exposing a human body to energy and to a method for the operation of such a device, in all cases in accordance with the preambles of the independent claims.

The present invention further relates to the use of vapour mixtures comprising at least one cannabinoid in devices for exposing a human body to energy, likewise in accordance with the preambles of the independent claims.

BACKGROUND

Cannabinoids and synthetic analogues thereof are pharmaceutically active secondary substances mainly obtainable from extracts of the hemp plant (Cannabaceae family). Most cannabinoids are varyingly psychotropic substances that act on the central nervous system and are associated inter alia with analgesic effects. Nowadays there is widespread medical acceptance of the use of cannabinoid-containing herbal medicinal substances used for alleviation of neuropathic and inflammation-related pain. Numerous studies have pointed to other possible indications, which are currently being intensively investigated, for example cannabinoids are being considered inter alia for the alleviation of the following symptoms: alleviation of spastic complaints, improvement of intestinal motility, antiemetic effects, lowering of intraocular pressure and numerous adjuvant effects in the treatment of psychological and psychosomatic disorders, such as anxiety disorders.

The licensing of *cannabis*-based medicaments for these therapeutic uses continues to grow. In most countries, cannabinoids are available on prescription only, approval for use in medical practice having been granted in particular for the treatment of chronic pain states, such as neuropathic pain or cancer pain, in spasticity and seizures, such as can be triggered by multiple sclerosis or other neurological conditions, or to treat nausea and loss of appetite associated with chemotherapies. Alongside medical use, the progressive liberalization of the consumption of *cannabis* products having reduced tetrahydrocannabinol contents as recreational substances has led to increasing acceptance of cannabinoids in general in western society.

The use of wellness devices is common practice as an accompaniment to therapeutic measures potentially associated with severe side effects for patients. Such devices are likewise used for alleviation of complaints caused by states of stress or when at least one beneficial effect can be achieved by measures to promote relaxation. For example, massages and light therapy can release stress, improve the circulation and, through a beneficial psychosomatic effect, pave the way to a relaxation process that is conducive to recovery.

Suitable devices can for example be light therapy apparatuses or solariums that emit dosed amounts of light and/or UV energy in order for example to eliminate seasonal mood changes in patients brought on by reduced exposure to sunlight. Therapies to release tension and antispasmodic therapies can likewise be selectively aided by massage apparatuses, for example dry massage apparatuses, that are able to selectively massage parts of the body by means of a closed jet of water.

There is thus a need for such treatment devices or wellness devices that are suitable both as an aid in the alleviation of psychosomatic complaints or as an adjuvant in therapeutic measures.

BRIEF DESCRIPTION OF THE INVENTION

It is thus an object of the invention to overcome at least one disadvantage of the prior art.

It is in particular an object of the invention to provide a device of the kind mentioned in the introduction that is suitable for carrying out a therapeutic treatment and/or a wellness therapy. For such purposes, the device should preferably be safe in use and enable exact dosing of the treatment parameters.

It is additionally an object of the present invention to provide an appropriate method for the operation of a device of the invention and to provide for the use in said devices of a vapour mixture comprising at least one herbal medicinal substance.

At least one of these objects is achieved by the features of the independent claims.

One aspect of the present invention relates to a device for exposing a human body to energy. The device includes a contact surface that defines an exposure area. A human body can be positioned in this exposure area such that it is within the coverage area of the energy.

The device also includes at least one means of emitting the energy essentially directed at the exposure area. In addition, the device includes at least one means of generating a vapour mixture comprising at least one cannabinoid.

In addition, the device of the invention includes at least one means of conveying the vapour mixture comprising an effective dose of at least one cannabinoid to the area surrounding the openings to the respiratory system of the human body.

For the purposes of the present invention, suitable cannabinoids can be understood as meaning not only those that can be extracted naturally from the cited plant family of the *cannabis* plants, in particular *Cannabis sativa* or *Cannabis indica*, but also analogues obtained by isomerization of appropriate precursors, for example from cannabidiol to tetrahydrocannabinol, and those produced synthetically. The most well-known cannabinoid is $\Delta^9$-tetrahydrocannabinol, which can be obtained from hemp plants by extraction. Methods of extraction are known to those skilled in the art.

For the purposes of the present invention, the area surrounding the openings to the respiratory system of the human body can be for example the head region of the human body, that is to say the area surrounding the nose and the mouth.

For the purposes of the present invention, a contact surface can be a lying surface that is essentially horizontal in design. Likewise possible is a contact surface that includes a seat or back rest in which the human body concerned can sit and/or recline. In one particular embodiment, the contact surface is a floor plate or standing surface on which the person can stand in the exposure area so that he/she is within the coverage area of the energy.

For the purposes of the present invention, the effective dose can be understood as meaning the dose of an active substance in a vapour mixture, and of a cannabinoid in particular, that achieves a desired pharmacological effect in a statistically relevant proportion of people. The desired pharmacological effect can be determined by those skilled in the art according to the therapeutic outcome to be achieved. For example, the effective dose, e.g. in devices of the invention used for recreational purposes in the context of wellness therapies, is set appropriately low in order that e.g. just muscle relaxation or a pleasurable sense of wellbeing is to be achieved. In medical/therapeutic uses, the effective dose can be chosen in respect of the therapeutic intent to be achieved. For example, the effective dose for different cannabinoids can vary according to the pharmacological effect. The corresponding effective doses are given in the legal guidelines and in the guidelines prescribed by the pharmacopoeia (see inter alia the Swiss Pharmacopoeia or European Pharmacopoeia). For the best investigated cannabinoids, for example THC, effective doses within a range of between 5 mg to 60 mg per day are specified, which are administered daily in tablet form. In the case of medicaments administered in liquid form, for example for the treatment of glaucoma, a THC concentration e.g. of between 1 to 7% is envisaged for single-dose daily treatment.

In one particular embodiment, the effective dose can be adjusted on the basis of an oil-based vaporization agent having a THC content of between 0.1% and 1% by volume and a cannabidiol content of between 10% and 20% by volume.

In one particular embodiment, the effective dose can be adjusted via the amount of cannabinoid in the vaporization agent, particularly when the effective dose is between 36% and 61% of the cannabinoid content of the vaporization agent in the vapour mixture. For example, during operation, the proportion of the cannabinoid from the vaporization agent that is available in the vapour mixture as the effective dose would be adjustable by those skilled in the art based on temperature and on the manner in which the vapour mixture is generated, for example by conduction, convection and/or through sonication.

In one particular embodiment of the present invention, the area surrounding the opening to the respiratory system of the human body is a defined area. This defined area can comprise, for example, a specific volume. It is then possible, based on this defined volume, for the user to adjust the appropriate effective dose in respect of the desired effect. For example, it is possible to establish with a vapour mixture a defined atmosphere that ensures it is possible to achieve the appropriate effective dose through inhalation of the vapour mixture in the area surrounding the opening to the respiratory system. This can increase the safety of the devices of the invention and in particular prevent unwanted side effects, for example psychotropic effects.

With the achievement of the present invention, a device as mentioned in the introduction is provided that is therapeutically safe and synergistically combines the beneficial effects of exposure to energy with treatment with herbal medicinal substances and that is able to optimally promote the therapeutic and/or wellness effect, particularly with a vapour mixture comprising an effective dose of a cannabinoid. Particularly by establishing a defined area surrounding the openings to the respiratory system, it is possible for safe administration of the appropriate effective dose to take place that prevents over-dosing leading e.g. to unwanted psychotropic side effects, or under-dosing that does not achieve the desired therapeutic effect.

In one particular embodiment, the means of emitting the energy essentially directed at the exposure area is designed to emit electromagnetic energy. Particularly preferably, the electromagnetic energy is radiation energy. Very particularly preferably, the radiation energy is UV radiation.

In one particularly preferred particular embodiment, the means of emitting the energy essentially directed at the exposure area is a light source. The light source may be fitted out for reflection of a particular colour spectrum. This may be accomplished by fitting the light source with appropriate filters.

Particularly preferably, the light source is capable of emitting light in the visible spectrum. This spectrum may comprise the range of between approx. 400 nm to approx. 1100 nm, in particular the range of between approx. 400 nm to approx. 750 nm.

In one particularly preferred embodiment, the light source includes filters that absorb and/or reflect harmful UV radiation. UV radiation in the region below 380 nm can in particular be harmful to health.

Particularly preferably, the light source is designed to reflect and/or absorb UV radiation in the range of between 200 and 380 nm.

In one particularly preferred embodiment, the light source is a solarium lamp. Solariums are largely used as wellness apparatuses intended to achieve for example tanning of the skin for cosmetic reasons or to achieve beneficial wellness effects through exposure to UV light. In medicine, solariums are used to treat certain skin diseases.

In one particular embodiment, the contact surface is a lying surface of a solarium unit for exposure to UV light while lying down.

In one further particular embodiment, the contact surface is a standing area of a standing solarium for exposure to UV light while standing up.

In one particularly preferred embodiment, the light source is an LED-based UV radiation source.

Solariums have been shown to treat seasonal mood changes, in particular to alleviate or eliminate altogether mood changes brought on by inadequate exposure to light. This therapy can be additionally improved by the device of the invention and the generation of an effective dose of a cannabinoid in the area surrounding the openings to the respiratory system during treatment. This can for example reduce the overall treatment time, which can overall help reduce the amount of radiation on the body.

In one particular embodiment, the means of emitting the energy essentially directed at the exposure area is designed to emit kinetic energy. Particularly preferably, the means is designed to emit a directed jet of fluid.

In one particular embodiment, the means of emitting the energy essentially directed at the exposure area is a jet nozzle that is designed to emit a jet of fluid, in particular a jet of water, at the exposure area. Such jet nozzles are user inter alia to eliminate muscular tension in a targeted and therefore gentle manner. This is done for example by directing a targeted jet of water of a defined intensity on a body part by means of a nozzle. Devices that enable treatment with jets of water in a dry state are also known.

The device for dry massage by means of jets of water (DE 20 2019 105 636 U1) includes one such dry massage device in which a waterproof cover is designed such that a body within the coverage area of the energy is not wetted by the jet of water; in other words, the water is hermetically retained by a water-impermeable membrane.

In one particular embodiment of the present invention, the means of generating a vapour mixture is a vaporizer.

For the purposes of the present invention, the vaporizer can be understood as meaning an apparatus for the vaporization of active substances. Such an apparatus allows active substances to be heated gently, in other words e.g. only to the necessary degree that they evaporate. Oxidation of the active substances can thus be prevented. Vaporizers for the consumption of recreational substances such as tobacco, *cannabis* or other herbs are known. Vaporizers are likewise known from medicine, for example in the field of anaesthesia, in order to generate defined effective doses of an anaesthetic active substance and convey them to the area surrounding the opening to the respiratory system of a human body. The vapour mixture can be generated using a composition that comprises a predetermined amount of the active substance. By adjusting the operating parameters for vaporization and feedback, e.g. with a defined area surrounding the openings to the respiratory system of the human body, it is possible to set an appropriate effective dose. In addition to the active substances, the compositions may comprise excipients, for example propylene glycol or glycerol. In addition to the cannabinoid, compositions that may be used according to the invention may also comprise other herbal medicinal substances suitable for vaporization, in particular a herbal medicinal substance selected from the group consisting of: lion's tail (*Leonotis leonurus*), ayahuasca (*Banisteriopsis caapi*), valerian (*Valeriana officinalis*), blue lotus (*Nymphaea caerulea*), damiana (*Turnera diffusa*), *eucalyptus* (*Eucalyptus globulus*), fly agaric (*Amanita muscaria*), hops (*Humulus lupulus*), Iceland moss (*Cetraria islandica*), St. John's wort (*Hypericum perforatum*), chamomile (*Chamomilla recutita*), kratom (*Mitragyna speciosa*), lavender (*Lavandula* spp.), purple passionflower (*Passiflora incarnata*), peppermint (*Mentha×piperita*), sage (*Salvia officinalis*), yarrow (*Achillea* spp.), sinicuichi (*Heimia salicifolia*), wild rue (*Peganum harmala*), thyme (*Thymus vulgaris*), sage of the diviners (*Salvia divinorum*), *yohimbe* (*Pausinystalia yohimbe*), and lemon balm (*Melissa officinalis*).

Particularly preferably, the composition comprises the cannabinoid $\Delta^9$-tetrahydrocannabinol ($C_{21}H_{30}O_2$). Suitable compositions can for example be obtained using pharmaceutically available dronabinol containing THC in amounts of between 1% and 2% by volume.

In one particular embodiment of the present invention, the means of conveying the vapour mixture comprising an effective dose of at least one cannabinoid to the area surrounding the opening to the respiratory system of the human body includes a retaining means, particularly preferably a retaining hood.

The retaining hood is preferably suitable for the generation in a vapour mixture of an effective dose of at least one cannabinoid in the area surrounding the openings to the respiratory system of the human body and the maintenance thereof. Particularly preferably, the retaining hood is designed with a defined volume. Very particularly preferably, the retaining hood is arranged in the coverage area of the energy such that the openings to the respiratory system of the human body are completely accommodated within the retaining hood. In one preferred embodiment, the retaining hood does not close completely, so that it is possible for gas exchange with the outside environment to take place. The retaining hood is preferably designed so that an atmosphere comprising the vapour mixture is able to form around the openings to the respiratory system of the human body, but in such a way that breathing out of the human body through the nose conveys the air exhaled from breathing outside the retaining hood. Particularly preferably, the retaining hood is closed at the crown region of the human head and open in the chin region, so that breathing out conveys the exhaled air outside the retaining hood.

In one particular embodiment, the retaining hood is coated on the inside. A possible coating would be a nanotexture, for example a nanotexture for generating a lotus effect that prevents the retaining hood from misting.

A retaining hood of such a design would advantageously have no adverse effect on the radiation energy passing through the retaining hood to which the body is then exposed. Such a retaining hood could find use for example in a solarium without the tanning effect on the user's head being limited thereby.

It has moreover surprisingly been found that, irrespective of the chemical structure of the cannabinoid and of THC ((−)-$\Delta^9$-trans-tetrahydrocannabinol) in particular, possible exposure to UV radiation does not result in any decomposition in the vapour mixture of the cannabinoids during the exposure period.

Suitable exposure periods can be between 1 min and 30 min, in particular between 5 and 15 min, very particularly preferably approx. 8 min.

In one particular embodiment, the retaining hood is designed to be essentially transparent to electromagnetic waves. Particularly preferably, it is transparent to electromagnetic waves in the wavelength regions between 380 nm and 1100 nm, further particularly between 380 nm and 750 nm. For this purposes, the retaining hood can be made for example from UV-transparent polymethyl methacrylate (plexiglas). Particularly preferably, at least the areas lying within the exposure area between the human body and the means of emitting the energy essentially directed at the exposure area are formed from a material that is essentially transparent to electromagnetic waves.

In one particular embodiment, the retaining hood is an integral part of the device for exposing a human body to energy. For example, the retaining hood can in the case of a solarium be a part of a lid element. A lid element can be a movable part of a solarium that, together with at least one contact surface, defines an area surrounding the openings to the respiratory system of the human body and the exposure area. In the case of standing solariums, it is possible for two lid elements to be provided.

In one particular embodiment, the device for exposing a human body to energy is a solarium having a lying surface as the contact surface and the retaining hood is an integral part of a lid element, such that a volume of between 450 $dm^3$ and 1000 $dm^3$, preferably between 580 $dm^3$ and 800 $dm^3$ is defined. This volume is preferably the area surrounding the openings to the respiratory system of the human body.

In one particular embodiment, the device for exposing a human body to energy is a solarium having a standing area as the contact surface and the retaining hood is an integral part of at least two lid elements, such that a volume of between 1000 $dm^3$ and 2000 $dm^3$, preferably of approx. 1100 $dm^3$ is defined. This volume is preferably the area surrounding the openings to the respiratory system of the human body.

Many solarium units are designed to be closable such that it is possible to enter a coverage area of exposure to light, the coverage area being defined by one or more lid elements in conjunction with the at least one contact surface. This type of solarium unit can be designed to be closable such that the entire inner volume therefore may be considered the area surrounding the openings to the respiratory system of the human body and can be filled with the appropriate vapour mixture.

In one particular embodiment, the retaining hood defines a volume of between 200 $dm^3$ and 400 $dm^3$, preferably of between 250 $dm^3$ and 350 $dm^3$, more preferably of approx. 275 $dm^3$. This volume is preferably the area surrounding the openings to the respiratory system of the human body.

The retaining hood can in one further embodiment be equipped with a pivot bearing so that is convertible from an open to a closed state.

In one particular embodiment, the retaining hood is designed so as to essentially prevent escape of the vapour mixture from the area surrounding the openings to the respiratory system of the human body. For this purpose, the retaining hood may be provided with suction openings or blowers that are able respectively to prevent escape of the vapours or aspirate escaping vapour mixture. Likewise possible is a retaining hood that is essentially conical in design, in which the vapour mixture collects at the tip of the cone as a consequence of the relatively higher temperature compared with the ambient air. At the end of treatment, the retaining hood can for example be aspirated.

In one particular embodiment, the device of the invention includes a storage tank for a vaporization agent comprising at least one cannabinoid.

In one further particular embodiment, the device includes a heating element for heating a defined amount of a vaporization agent such that a vapour mixture comprising a defined amount of the at least one cannabinoid can be formed.

In one particular embodiment, the heating element may be designed such that it acts directly on the vaporization agent. Alternatively and/or in addition, the heating element may be designed such that it acts indirectly on the vaporization agent.

In one particular embodiment, the heating element is designed for heating a vaporization agent by conduction.

In one additional and/or alternative embodiment, the heating element is designed for heating the vaporization agent by convection.

In one alternative and/or additional embodiment, the generation of the vapour mixture comprising a defined amount of the at least one cannabinoid takes place without heating. This can be accomplished for example by mixing an air flow with a saturated atmosphere comprising the appropriate cannabinoid. Alternatively and/or in addition, an ultrasonic nebulizer may be provided for generating the vapour mixture.

In one particular embodiment, the vaporization agent comprising at least one cannabinoid is a solid- or liquid-based composition suitable for an inhalational administration form comprising the at least one cannabinoid. Suitable solid- or liquid-based vaporization agents are known. The vaporization of the cannabinoid can take place either directly from the liquid phase or via sublimation directly from a base.

In one particular embodiment, the heating element is designed to achieve a temperature range of between 100° C. and 235° C. for the generation of the vapour mixture. Particularly preferably, the heating element is designed for a temperature range of between 165° C. and 200° C., very particularly preferably of approx. 200° C.

In one particular embodiment, the vaporization agent comprises additional excipients besides the active substance/herbal medicinal substance/cannabinoid.

In one particular embodiment, these excipients are excipients selected from the group consisting of: propylene glycol, glycerol, water, dexpanthenol, other aromatic and/or non-aromatic oils, aromas or substances regulating the viscosity of the vaporization agent.

In one particular embodiment, the device includes at least one fan for generating an air flow in the area surrounding the openings to the respiratory system of the human body. Particularly preferably, the air flow is designed for extraction of the vapour mixture comprising an effective dose of at least one cannabinoid from a retaining hood. In this embodiment, the fan may serve for the supply of fresh air in the area surrounding the openings to the respiratory system, in particular in the retaining hood.

Alternatively and/or in addition, the fan may be designed to free the retaining hood and area surrounding the openings to the respiratory system of the vapour mixture comprising the at least one cannabinoid at the end of the therapy session and/or wellness session. Such removal can ensure that the treatment time is not exceeded and that an effective dose is administered only over a particular defined period. This period can particularly preferably be synchronized with the exposure to energy. Thus, a therapy session and/or wellness session is accordingly able to gain optimal benefit from the synergy between the exposure to energy, such as dry massage with a jet of water or irradiation with UV radiation, and the desired therapeutic use of the cannabinoid.

In one particular embodiment, the device of the invention includes at least one optoelectronic sensor. Particularly preferably, this optoelectronic sensor is designed for the determination of at least one photoelectrically measurable physiological parameter of the human body in the coverage area of the energy. For example, the optoelectronic sensor may be a sensor for optical pulse measurement. Alternatively and/or in addition, the optoelectronic sensor may also be a UV sensor that measures for example the amount of UV radiation absorbed or the intensity of this UV radiation.

In one particular embodiment, sensors can be designed to control the operating parameters of the device. This would allow e.g. control and regulation of the individual parameters of the device over a treatment period. For example, in a dry massage device equipped with a retaining hood and a device for generating a vapour mixture comprising an effective dose of cannabinoid, the desired therapeutic effect could be adjusted for example on the basis of a particular target blood flow in the surface tissue. The appropriate effective dose is variably set so that it is in suitable agreement with the exposure to kinetic energy through the massage bed, in order to achieve an appropriate target value, which is measured by the optoelectronic sensor and adjusted via a control unit through direct control of the massage nozzles and/or of the means of generating a vapour mixture in the area surrounding the openings to the respiratory system of the human body.

In one particular embodiment, the device of the invention includes a control that regulates and/or controls the operating parameters of the means of generating the vapour mixture and of the means of emitting the energy essentially directed at the exposure area. This control unit can be additionally designed to receive measured data from sensors, for example the optoelectronic sensor as described above, and to evaluate these data and convert them into appropriate control signals with which the desired effect is to be achieved.

In one particular embodiment, the device of the invention is a bioelectronic sensor. Particularly preferably, the bioelectronic sensor is a sensor suitable for the measurement of resistance. Sensors of this kind are already in use for the measurement of resistances in the body, e.g. for the determination of respiratory rates and/or of body fat percentages.

In one particular embodiment, the means of conveying a vapour mixture comprising an effective dose of at least one cannabinoid to the area surrounding the openings to the respiratory system of the human body includes an inlet opening that feeds vapour mixture generated outside a retaining hood into the interior of the retaining hood.

In one particular embodiment, the retaining hood is essentially cup-shaped in design, so that it is suitable for at least partially enclosing at least part of the head and/or of the upper body of a human body undergoing treatment with the device of the invention. Particularly preferably, the retaining hood is designed as a receptacle suitable for retaining an appropriate atmosphere comprising an effective dose of at least one cannabinoid for a particular period.

In one particular embodiment, the means of conveying a vapour mixture comprising an effective dose of at least one cannabinoid to the area surrounding the openings to the respiratory system of the human body includes at least one outlet opening. Particularly preferably, the outlet opening is connected to a suction device. The outlet opening may be designed to evacuate an appropriate atmosphere. This may involve the outlet opening also being operatively connected to a fan, as described further above, by means of the presence e.g. of a hose connection between the outlet opening and the fan.

A further aspect of the present invention relates to a method for the operation of a described device. The method includes the step of providing a device for exposing a human body to energy. Particularly preferably, the device is one having any not mutually exclusive combination of features of the device of the invention described above. In addition, a vaporization agent comprising at least one vaporizable herbal medicinal substance is provided. Particularly preferably, the herbal medicinal substance is a cannabinoid. The method additionally includes the step of vaporizing the vaporization agent such that this results in the formation of a vapour mixture comprising an effective dose of the at least one herbal medicinal substance. Particularly preferably, a vapour mixture comprising an effective dose of at least one cannabinoid is formed.

The vapour mixture is conveyed to the area surrounding the opening to the respiratory system of a human body. This can be accomplished by providing e.g. appropriate hose connections and/or inlet openings that feed a generated vapour mixture into the part of the exposure area in which the openings to the respiratory system of the human body are positioned. Particularly preferably, the vapour mixture is conveyed thus to the area surrounding the openings to the respiratory system of the human body such that the effective dose of the at least one cannabinoid is formed inside a retaining means. Particularly preferably, the retaining means is a retaining hood.

The method of the invention may additionally include the step of regulating, controlling and/or adjusting the vaporization of the vaporization agent in an exposure routine that is generated by the device.

There may also be provision in the method of the invention e.g. for measurement or detection of a particular parameter. For example, use may be made of e.g. a given physiological state for regulation of an effective dose. In one specific embodiment, the effective dose could be defined within a particular range that represents a permitted range within which a given physiological value is to be attained. For example, a vapour mixture may be provided e.g. with an effective dose of a cannabinoid, said dose comprising between 5 mg and 15 mg of THC. The exact amount in the effective dose is made dependent on a given physiological parameter that is measured by the sensors and signalled to the control unit. If the physiological parameter is attained, the effective dose is not increased. The device can in this specific example be designed to increase the effective dose in a stepwise manner. In the specific example, this could mean that an agent provided for convective heating of a vaporization agent bypasses the air flow to the vaporization agent for as long as it takes, in this form, for the desired effective dose to be reached/until the sensor signals the physiological parameter to be attained to the control unit. To prevent a further increase in the effective dose, a bypass can for example be provided, in which the air flow is then no longer fed past the evaporation agent and thus further THC does not reach the area surrounding the airways, i.e. the retaining hood in the specific example.

A further aspect of the present invention relates to the use of vapour mixtures comprising at least one cannabinoid in devices for exposing a human body to energy. This is accomplished by conveying a vapour mixture comprising an effective dose of at least one cannabinoid to the area surrounding the openings to the respiratory system of a human body.

There has been found to be a synergistic effect between devices for exposing a human body to energy and the use of vapour mixtures comprising at least one cannabinoid. In wellness therapies in particular, low-dose cannabinoid concentrations in the area surrounding the openings to the respiratory system of the human body are able to achieve a heightened relaxation effect and a boost to a person's general wellbeing.

The present invention is additionally also suitable for the medical-therapeutic sector. The spectrum of treatment can range from therapeutic methods for the alleviation of side effects and pain to the amelioration of psychosomatic complaints.

In one particular embodiment, the use according to the invention includes the use of an effective dose of at least one cannabinoid in the form of a vapour mixture in association with exposing a person to light to alleviate psychosomatic complaints and to boost general wellbeing.

In one further embodiment, the use according to the invention involves the use of a vapour mixture comprising at least one cannabinoid in combination with exposing the patient to kinetic energy, for example with a jet of water from a massage nozzle, preferably a dry massage device of the kind described in the introduction, to alleviate psychosomatic complaints and to boost general wellbeing.

In one particular embodiment, the psychosomatic complaints comprise seasonal mood states, such as those that can occur in the winter months. Seasonal mood changes in the winter months have been shown to be attributable to inadequate sunlight. It has surprisingly been found that combination treatments with a cannabinoid and appropriate exposure, for example to ultraviolet light, can significantly alleviate psychosomatic complaints associated with seasonal mood changes effectively and with just short sessions of treatment.

In one particular embodiment, the use according to the invention involves a retaining hood that is suitable for the generation of an effective dose of the at least one cannabinoid in the area surrounding the openings to the respiratory system of the human body and the maintenance thereof.

For the purposes of the present invention, the use of the at least one cannabinoid also includes synthetic analogues, for example dimethylheptylpyran (DMHP).

In one particular embodiment, the use involves a vaporization agent having a particular concentration of a cannabinoid. This vaporization agent may also be generated using herbal extracts from the *cannabis* plant. Alternatively and/or in addition, the direct use of parts of the *cannabis* plant is also suitable in order to generate a vaporization agent having the appropriate content of active substance. Particularly suitable for this purpose are pharmacognostically determined and standardized herbal medicinal substances comprising parts of the *cannabis* plant. For example, the finely ground powder from flowers of the *cannabis* plant (*Cannabis flos*) is particular suitable.

Almost all exogenous cannabinoids are in principle suitable for use according to the invention. Up to 70 cannabinoids in total are known. The effective dose can be tailored to the desired effect. For example, at a low dosage an analgesic and sometimes sedative-hypnotic effect can be achieved. After overdosage or after a very high dose, states of altered consciousness can develop. Those skilled in the art will be familiar with the effective doses for treating increased intraocular pressure, pain, hypertension, nausea, poor appetite, or even as an appetite suppressant.

The use according to the invention can in one particular embodiment involve the use of electromagnetic energy, in particular radiation energy. In this use, the effective dose of the at least one cannabinoid is administered in combination with radiation treatment, particularly preferably UV radiation treatment. This combination has proved particularly advantageous in the treatment of seasonal mood swings.

In one further particular embodiment, the use according to the invention involves the use of kinetic energy. Particularly preferably, the kinetic energy is employed in the form of a directed fluid jet. This can be accomplished for example by a jet of water directed from a nozzle in a targeted manner onto a part of the body of the individual undergoing treatment. Water massage apparatuses of this kind are known. The water massage apparatuses used are particularly preferably ones with which the body does not get wet, i.e. suitable for dry massage. Such apparatuses have a membrane that retains the jet of water, but is to a certain degree able to transfer the kinetic energy to the human body through deformation of the membrane.

It has surprisingly been found that the use of such massage apparatuses in association with the administration of an effective dose of a cannabinoid is particularly suitable for the alleviation of muscular tension, states of stress and circulation-related hardening of the musculature.

To those skilled in the art, it goes without saying that a realization in accordance with the invention of the described device, of the corresponding method and of the corresponding use is able to achieve any combination of the described features, provided these are not mutually exclusive. Further advantageous features will be discernible to those skilled in the art hereinbelow from the detailed description and from the specific embodiments.

The present invention is elucidated in more detail hereinbelow with reference to specific figures and exemplary embodiments, without being restricted thereto.

BRIEF DESCRIPTION OF THE DRAWINGS

Exemplary embodiments of the invention are described with reference to the figures below. In these figures

DETAILED DESCRIPTION OF THE INVENTION

Figure 1:
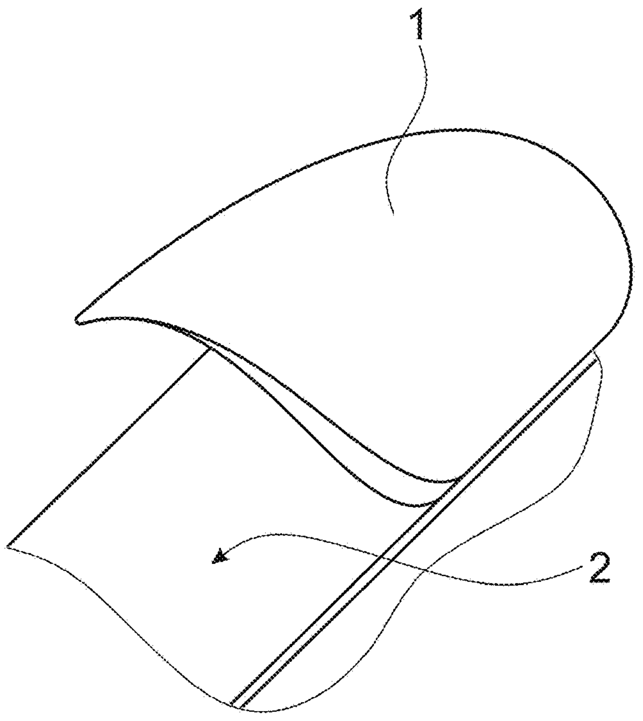
FIG. 1 shows a device of the invention.

FIG. 1 shows a particularly simple embodiment of a device of the invention. Arranged at a head end of a contact surface 2, which in the present example is designed as a lying surface, is a retaining hood 1.

The retaining hood 1 can in the present case be opaque in design, e.g. made of a plastic material. For the present use it may be advantageous when the retaining hood 1 additionally causes slight darkening of the head area. The retaining hood 1 is closed in the crown region and opens downwards towards the lower body. The chosen dimensions of the present embodiment are such that the head and shoulders of a person lying on the contact surface 2 are inside the retaining hood 1, whereas the limbs and the upper body lie outside the retaining hood.

The contact surface 2 may in the present example take the form of a membrane. The membrane may seal off a liquid-filled space in which jet nozzles are arranged that are suitable for directing a jet of water onto the contact surface, such that said membrane at the same time defines an exposure area. During operation, a user would be lying on the contact surface and exposed to kinetic energy through said membrane, by means of jets of water. During this time, his/her head would be lying beneath the retaining hood 1. The retaining hood 1 may be furnished e.g. (not shown in the present example) with LED illumination to aid relaxation. For example, strips of red LEDs in the interior or around the edge of the retaining hood can create a subdued, warm atmosphere conducive to relaxation.

The retaining hood may be provided with inlet openings (likewise not shown). Through these inlet openings can be fed a vapour mixture comprising an effective dose of at least one cannabinoid. If the patient is now lying with his/her head beneath the retaining hood, a controlled atmosphere develops around the head that enables the administration to the patient of a defined effective dose of a cannabinoid. In the present example, the retaining hood is convex in design, such that it defines a volume in which the vapour mixture may be present.

With the device of the invention. as shown in FIG. 1, it is possible e.g. for a wellness unit for the treatment of psychosomatic complaints such as seasonal mood changes or muscular tension to be used. Depending on the planned use, those appropriately skilled in the art can define the composition of a vapour mixture and specify the corresponding effective dose needed in order to achieve the desired therapeutic or sedative effect.

Figure 2:
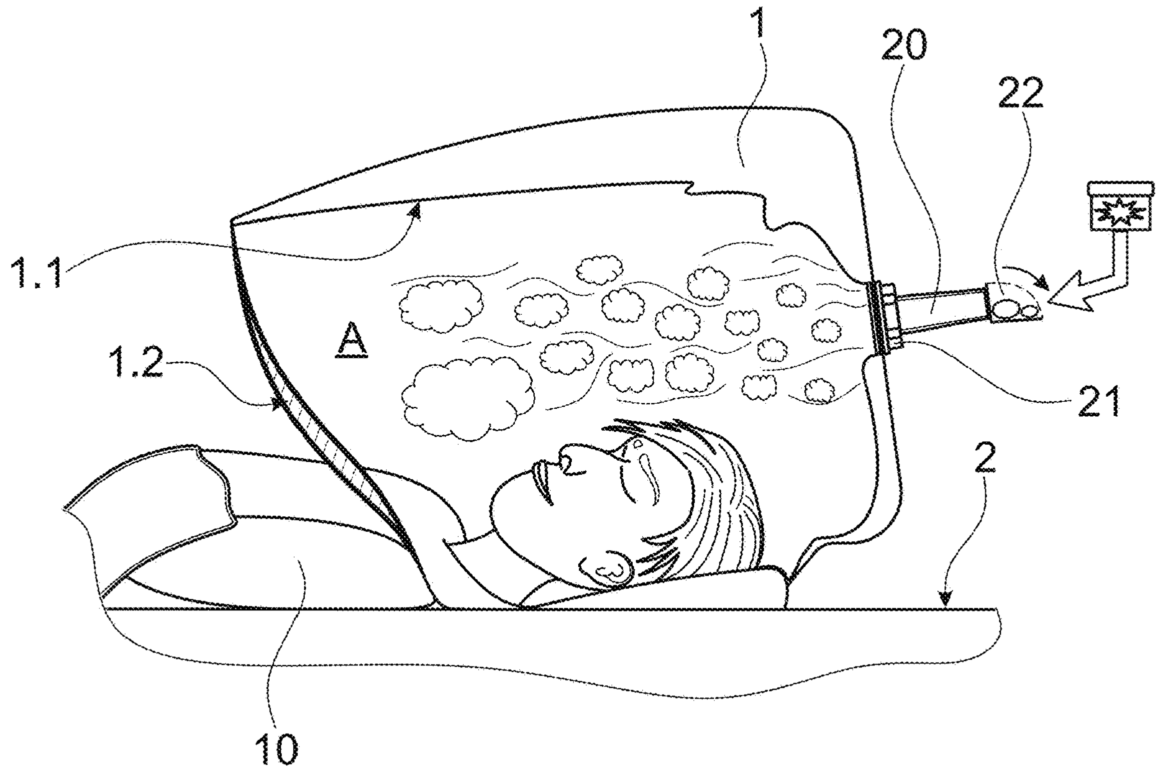
FIG. 2 shows the device of the invention from FIG. 1 in use.

This is explained in more detail in the example in FIG. 2, which provides a schematic representation in use of the device of the invention shown in FIG. 1.

A contact surface 2 is also provided, on which a patient 10 can lie down. Over the head of the patient 10 can be positioned a retaining hood 1, which defines an area surrounding the openings to the respiratory system A as a volume. The retaining hood 1 is furnished on the inside 1.1 with light-emitting diodes intended to enhance the relaxation effect. It is also possible for the retaining hood 1 to have a coating intended to prevent condensation of water vapour inside the retaining hood. Condensed water vapour could result in droplet formation, which would be undesirable for the relaxation effect in the present example. It would also be possible for the retaining hood 1 to be provided with cooling and/or heating elements either to create an appropriate atmosphere or to prevent condensation from forming. The retaining hood 1 is in the distal region, i.e. it can be ventilated through an opening 1.2 towards the extremities.

Gas exchange with the surroundings results in the effective dose decreasing over time if the vapour mixture is not replenished. The vapour mixture is fed into the retaining hood 1 via a supply connector 20. The vapour mixture is in the present example generated through a convective vaporization process. This is accomplished by circulating a warm air flow around a vaporization agent 22 at a predefined temperature so that the desired amount of vaporization agent 22 vaporizes and is conveyed into the retaining hood 1 via a supply connector 20 and the outlet opening 21.

Although the retaining hood is in the present case opaque in design, it can of course also be transparent in design in this use.

During operation, a heating element (not shown) would be circulating air heated to an operating temperature of between 130° Celsius and 226° Celsius around a defined amount of a vaporization agent, e.g. a mixture comprising 1.7 mg of finely ground *cannabis*, so that a vapour mixture forms. Particularly suitable is a temperature of approx. 185° Celsius. The *cannabis* used in the present example has a content of at least tetrahydrocannabinol (THC), cannabidiol (CBD) and cannabinol (CBN). The THC content in the standardized mixture is between 3.5 and 4.5%, preferably 4.15%. CBD and CBN are present in traces. The water content in the present example is approx. 10% to 15% by weight (see also Gieringer, D., et al.; *Cannabis* Vaporizer Combines Efficient Delivery of THC with Effective Suppression of Pyrolytic Compounds; Journal of *Cannabis* Therapeutics, October 2008).

A *cannabis* vapour resulting therefrom can have a THC content of between 36 and 61%. On the basis of these data, those skilled in the art are able to generate an effective dose of a vapour mixture in a targeted manner based on a volume in the area surrounding the openings to the respiratory system of a patient.

Figure 3:
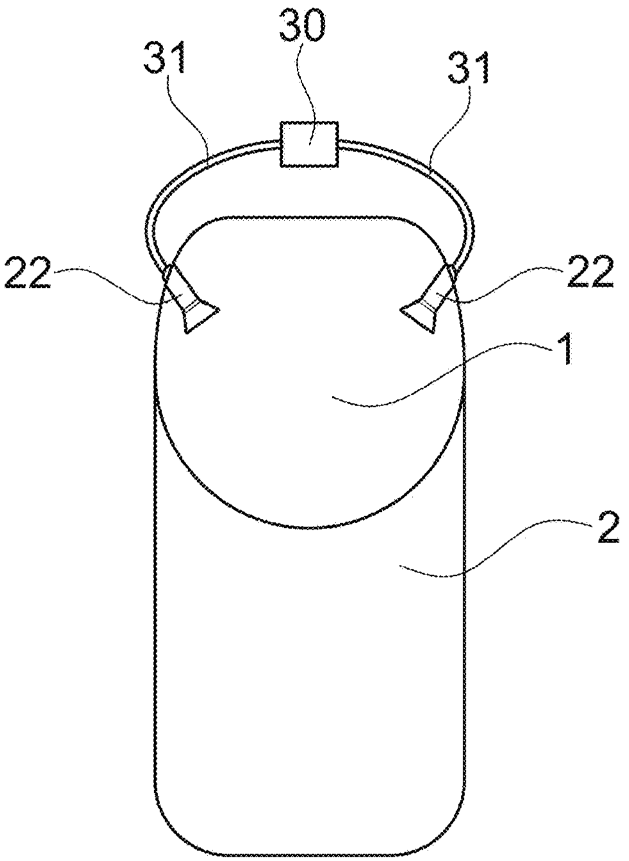
FIG. 3 shows a further embodiment of the device of the invention.

FIG. 3 shows a schematic representation of a device of the invention having a contact surface 2 and an appropriately designed retaining hood 1, showing how they may be supplied, by means of two supply connectors 20 connected by hose connections 31 to a vaporizer 30, with an appropriate vapour mixture comprising an effective dose of a cannabinoid.

Figure 4:
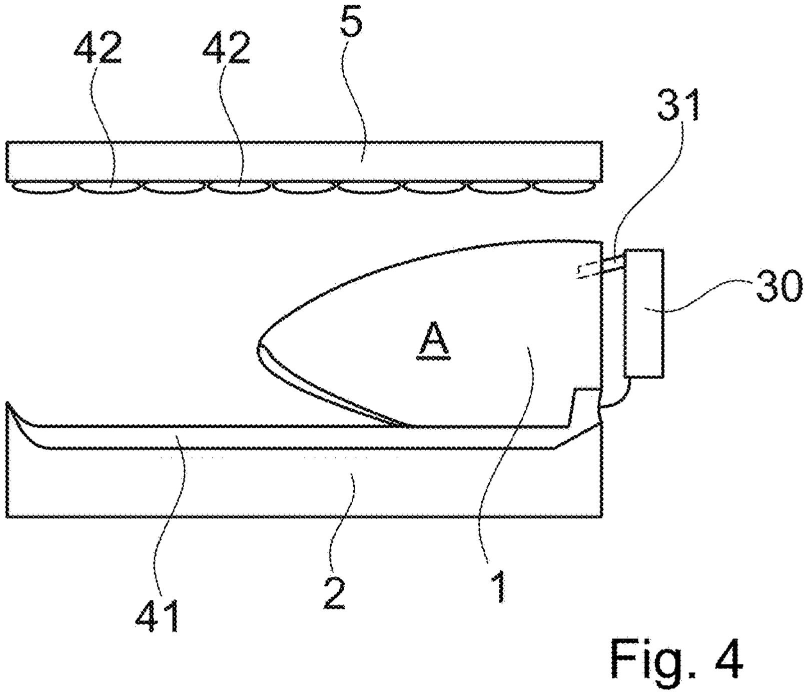
FIG. 4 shows a further embodiment of the device of the invention.

An appropriate embodiment for an irradiation device is shown in FIG. 4. The design shown in FIG. 4 likewise includes a contact surface, on which a patient can lie down. Unlike in the previous embodiment, the contact surface is there solely for the specific purpose of orienting the patient for the exposure to energy. The contact surface 2 and a facing lid surface 5 are appropriately provided with light sources 42, 41 that form an exposure area on which the patient is exposed to light. In a solarium, these would accordingly be UV lamps. Extending in this exposure area is a retaining hood 1 that defines an area surrounding the openings to the respiratory system of the patient A. This retaining hood 1 is connected to a vaporizer by means of a hose connection 31. The vaporizer uses a suitable method, for example conductive heating of a vaporization agent, to generate an appropriate vapour mixture that is channeled through the hose connection 31 into the retaining hood 1. In the present example, the retaining hood is of course transparent in design, made for example from a UV-permeable polymethyl methacrylate, such as those used by way of example for greenhouses as plexiglas under the trade name Alltop®. Likewise particularly suitable is SUNACTIV GS 2458 plexiglas.

Figure 5:
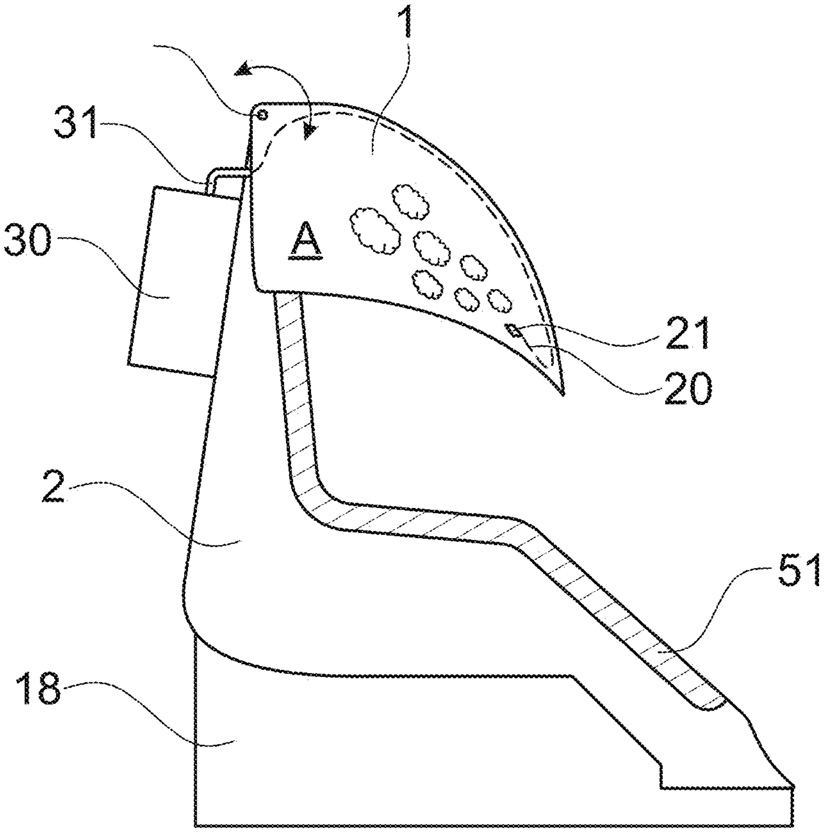
FIG. 5 shows a further embodiment of the device of the invention.

An alternative embodiment is shown in FIG. 5, in which the device is conceived for seated use.

In this device too, the energy is kinetic energy and exposure takes place by means of massage elements.

Accordingly, the contact surface 2 is provided with an appropriate mechanical massage device 51, such as a rotating massage stick. This too can be integrated into a membrane so as to enhance comfort during therapy. The device stands on a plinth 18. During operation, the patient sits on the massage stick 51 and an, in this case foldable, retaining hood 1 is closed over the patient's head such that the area surrounding the openings to the respiratory system A forms a defined area. A vapour mixture in a vaporizer 30 is fed to the patient via hose connections 31 into this surrounding area A by means of a supply connector 20 and a nebulizer 21.

What is claimed is:

1. Device configured to expose a human body to energy, wherein the energy comprises electromagnetic and/or kinetic energy, comprising:

a. a contact surface that defines an exposure area in which a human body can be positioned within a coverage area of the energy;

b. at least one means of emitting the energy essentially directed at the exposure area, at least one means of generating a vapour mixture comprising at least one cannabinoid, and at least one means of conveying the vapour mixture comprising a dose of the at least one cannabinoid to an area surrounding the openings to a respiratory system of the human body, wherein the means of conveying a vapour mixture includes;

a retaining hood, having a closed portion configured to be positioned above a crown region of a head of the human body and an open portion configured to be positioned such that the open portion extends past a chin region of the human body, a vaporizer configured to circulate a warm air flow around a vaporizing agent at a predefined temperature so that vaporizing agent vaporizes into the flow of warm air to form the vapour mixture, a supply connector configured to convey the vapour mixture to an outlet opening, wherein the outlet opening is connected to the closed portion of the retaining hood above the crown region of the head of the human body, such that the vapour mixture flows from the head of the human body towards the chin of the human body, wherein the retaining hood extends in the exposure area and at least the areas of the retaining hood lying within the exposure area between the human body and the means of emitting the energy essentially directed at the exposure area are transparent to electromagnetic waves, and wherein the retaining hoodessentially prevents escape of the vapour mixture from the area surrounding the openings to the respiratory system of the human body.

2. Device according to claim 1, wherein the means of emitting the energy essentially directed at the exposure area is designed to emit electromagnetic energy.

3. Device according to claim 1, wherein the means of emitting the energy essentially directed at the exposure area is designed to emit a directed jet of fluid.

4. Device according to claim 1, wherein the means of generating the vapour mixture is a vaporizer.

5. Device according to claim 1, wherein the retaining hood is suitable for the generation in the vapour mixture of the dose of the at least one cannabinoid in the area surrounding the openings to the respiratory system of the human body and the maintenance thereof.

6. Device according to claim 1, including a storage tank for a vaporization agent comprising at least one cannabinoid and a heating element for heating a defined amount of the vaporization agent such that the vapour mixture comprising a defined amount of the at least one cannabinoid forms.

7. Device according to claim 1, including at least one fan for generating an air flow in the area surrounding the openings to the respiratory system of the human body.

8. Device according to claim 7 wherein the air flow is configured for extraction of the vapour mixture comprising a dose of at least one cannabinoid from the retaining hood.

9. Device according to claim 1, including at least one optoelectronic sensor.

10. Device according to claim 9 wherein the optoelectronic sensor is configured for the determination of at least one photoelectrically measurable physiological parameter of the human body in the coverage area of the energy.

11. Device according to claim 1, including at least one bioelectronic sensor.

12. Device according to claim 11 wherein the at least one bioelectric sensor is configured for the measurement of resistance.

13. Device according to claim 1, wherein the means of conveying the vapour mixture comprising the dose of the at least one cannabinoid to the area surrounding the openings to the respiratory system of the human body includes an inlet opening that feeds vapour mixture generated outside the retaining hood into said hood.

14. Device according to claim 1, wherein the means of conveying the vapour mixture comprising the dose of the at least one cannabinoid to the area surrounding the openings to the respiratory system of the human body includes an outlet opening.

15. Device according to claim 14 wherein the outlet opening is connected to a suction device.

16. Method for the operation of a device according to claim 1 for non-therapeutic recreational purposes on a healthy person, comprising the steps of:

a. providing a device for exposing a human body of the person to energy according to claim 1;

b. providing a vaporization agent comprising at least one vaporizable herbal medicinal substance comprising at least one cannabinoid;

c. vaporizing the vaporization agent using the means of generating a vapour mixture such that this results in the formation of a vapour mixture comprising a dose of the at least one herbal medicinal substance;

d. conveying the vapour mixture using the means of conveying the vapour mixture to the area surrounding the openings to the respiratory system of the human body.

17. Method according to claim 16, wherein the device includes a control, and wherein operating parameters of the means of generating the vapour mixture and of the means of emitting the energy essentially directed at the exposure area are regulated and/or controlled.

18. Method according to claim 17, wherein the device includes at least one sensor and the method further comprises the steps of:

a. the control receiving measured data determined by the sensor;

b. evaluating the measured data in respect of one or more operating parameters; and c. converting the evaluation into one or more control signals for regulating the one or more operating parameters.

19. Method according to claim 16 wherein the vapour mixture comprises a dose of at least one cannabinoid.

20. Method according to any one of claim 16 wherein the conveying is performed such that the dose of at least one cannabinoid is formed inside the retaining hood.

* * * * *